(12) United States Patent
DiMartino et al.

(10) Patent No.: US 9,439,835 B2
(45) Date of Patent: Sep. 13, 2016

(54) BIOMETRIC ELECTRONIC COMMUNICATING DRUG DISPENSER

(75) Inventors: Christopher J. DiMartino, Richmond, VA (US); Richard Graham, Norwich, VT (US)

(73) Assignee: MEDICATION CONTROL SYSTEMS, LLC, Orlando, FL (US)

( * ) Notice: Subject to any disclaimer, the term of this patent is extended or adjusted under 35 U.S.C. 154(b) by 95 days.

(21) Appl. No.: 13/612,568

(22) Filed: Sep. 12, 2012

(65) Prior Publication Data

US 2013/0088328 A1    Apr. 11, 2013

Related U.S. Application Data

(60) Provisional application No. 61/533,538, filed on Sep. 12, 2011.

(51) Int. Cl.
| | |
|---|---|
| G08B 21/00 | (2006.01) |
| A61J 7/00 | (2006.01) |
| A61J 7/04 | (2006.01) |
| G06F 19/00 | (2011.01) |

(52) U.S. Cl.
CPC ............. *A61J 7/0076* (2013.01); *A61J 7/0481* (2013.01); *G06F 19/3462* (2013.01); *A61J 2200/30* (2013.01); *A61J 2200/70* (2013.01); *A61J 2205/70* (2013.01)

(58) Field of Classification Search
CPC .................. G06F 19/3462; A61J 2007/0418; A61J 2200/30; A61J 7/0481; A61J 2007/0454
USPC ............. 340/573.1, 5.53, 540; 700/215, 235, 700/241, 242; 600/301; 705/3
See application file for complete search history.

(56) References Cited

U.S. PATENT DOCUMENTS

| | | | |
|---|---|---|---|
| 3,874,564 A * | 4/1975 | Huneke ......................... | 222/363 |
| 2006/0089545 A1 | 4/2006 | Ratjen et al. | |
| 2006/0184271 A1* | 8/2006 | Loveless ....................... | 700/231 |
| 2007/0186923 A1 | 8/2007 | Poutiatine et al. | |
| 2008/0086326 A1* | 4/2008 | Moura et al. .................... | 705/2 |
| 2008/0114490 A1* | 5/2008 | Jean-Pierre ................... | 700/241 |

(Continued)

FOREIGN PATENT DOCUMENTS

| | | |
|---|---|---|
| JP | 2003-528652 | 9/2003 |
| JP | 2006-520659 A | 9/2006 |

(Continued)

OTHER PUBLICATIONS

The Notification of Transmittal of the International Search Report and the Written Opinion of the International Searching Authority, or the Declaration issued Mar. 4, 2013 in the Corresponding PCT Application No. PCT/US2012/054920, filed Sep. 12, 2012.
Office Action issued in related JP2014529991 dated Apr. 12, 2016.

*Primary Examiner* — Mark Rushing
(74) *Attorney, Agent, or Firm* — McGuireWoods LLP

(57) ABSTRACT

A system, a device, a method, and a computer program are provided that dispense pharmacy/clinic loaded medications only to a specific patient that has biometric information pre-programmed to a Biometric Electronic Communicating Drug Dispenser (BECDD) device by, e.g., a clinic physician or authorized user. The biometric information may include, e.g., a finger print, a retinal signature, a voice signature, a DNA code, a blood type, or the like.

19 Claims, 12 Drawing Sheets

(56) References Cited

U.S. PATENT DOCUMENTS

| | | |
|---|---|---|
| 2008/0119958 A1* | 5/2008 | Bear et al. ............... 700/244 |
| 2008/0179387 A1* | 7/2008 | Cantlay ............. A61J 7/0481 235/375 |
| 2009/0219135 A1* | 9/2009 | Harvey ............ B60R 25/2018 340/5.82 |
| 2009/0315702 A1* | 12/2009 | Cohen Alloro et al. ... 340/539.1 |
| 2010/0228566 A1 | 9/2010 | Taylor et al. |
| 2011/0060457 A1* | 3/2011 | De Vrught et al. .......... 700/241 |
| 2012/0029693 A1* | 2/2012 | Bear et al. ................... 700/244 |
| 2013/0131586 A1 | 5/2013 | Poutiatine et al. |

FOREIGN PATENT DOCUMENTS

| | | |
|---|---|---|
| JP | 2009-526553 A | 7/2009 |
| KR | 10-2010-0039865 | 4/2010 |

\* cited by examiner

BIOMETRIC ELECTRONIC COMMUNICATING DRUG DISPENSER

CROSS-REFERENCE TO PRIOR APPLICATIONS

This application claims priority under 35 U.S.C. §119(e) to U.S. Provisional Patent Application No. 61/533,538, filed Sep. 12, 2011, titled "BIOMETRIC ELECTRONIC COMMUNICATING DRUG DISPENSER," the disclosure of which is hereby expressly incorporated herein by reference in its entirety.

FIELD OF THE DISCLOSURE

The present disclosure relates to a system, a device, a method, and a computer program for dispensing drugs.

BACKGROUND OF THE DISCLOSURE

An unfulfilled need exists for a solution for non-compliant patients, medication errors, prescription medication abuse, medication thefts, and inaccurate reporting. Transplant patients, drug study patients, elderly patients, non-compliant patients, Alzheimer patients, clinics, physicians, are need of a device that can notify a patient that it was time for their medication, and at the same time generate a record of the event. Further, an unfulfilled need exists for device that would prevent and/or reduce prescription drug abuse, unauthorized access to patient medications, theft, accidental overdose, forgotten dose, and increase patient compliance.

The disclosure provides a system, a device, a method and a computer program that fulfill the aforementioned needs.

SUMMARY OF THE DISCLOSURE

According to one non-limiting example of the disclosure, a system, a device, a method, and a computer program are provided that dispense pharmacy/clinic loaded medications only to a specific patient that has biometric information pre-programmed to a Biometric Electronic Communicating Drug Dispenser (BECDD) device by, e.g., a clinic physician or authorized user. The biometric information may include, e.g., a finger print, a retinal signature, a voice signature, a DNA code, a blood type, or the like.

The BECDD device is a secure portable drug/pill device that is designed to dispense pharmacy/clinic loaded medications only to a specific patient that has their biometric information pre-programmed into the BECDD device by, e.g., a clinic physician or authorized user. The BECDD device is configured to reproduce a notification to a patient in the form of, e.g., an audible, a vibration, or a display (e.g., a flashing light). The BECDD device is also configured to receive a patient dosage request and to dispense the exact prescribed dose of medicine to the patient.

The notification may be reproduced in response to a prescheduled drug delivery time, or in response to a dose delivery signal that may be received from a Delivery Control and Monitoring Station (DCMS), which may be operated by, e.g., a clinic, a physician, a hospital, or the like. The drug delivery time may include a date, a time, a day of week, or the like. The BECDD device may be configured to dispense a predetermined dosage to the patient.

The DCMS may include a computer that is configured to bidirectionally communicate with the BECDD device.

If the patient fails to access the medication, additional notifications may be reproduced by the BECDD device to alert the patient. Additionally, the BECDD device may send a failure to access medication signal to the DCMS. Upon receiving the failure to access medication signal, the DCMS may log the event, including, e.g., the BECDD device identification, the patient name, the event date, the event time, the medication in the BECDD device, the prescribed dosage, and the like.

The BECDD (or DCMS) may also be configured to send a notification signal in the form of e.g., a text message, a voice message, an email, or the like, to the patient, a family member, a care provider, or the like. The notification signal may include the failure to access medication signal, or it may include success to access medication signal, which may include, e.g., the BECDD device identification, the patient name, the dispensing date, the dispensing time, the dispensed medication, the dispensed dosage, and the like.

The BECDD device comprises both mechanical and electronic components, as well as firmware and software. The BECDD device contains a mechanical mechanism that holds and dispenses the medication via an actuator (such as, e.g., an electrical motor) that receives commands from a driver that operates under the control of a controller. The controller may include a computer.

The BECDD device includes a hidden locking mechanism that can only be opened by, e.g., a pharmacist, a clinic, a physician, or the like, using a special key. The BECDD device may be constructed in various shapes, sizes, and colors.

The outside of the BECDD device may be provided with a biometric sensor, a display, one or more actuators, one or more electronic ports, and the like. The biometric sensor may include, e.g., a fingerprint scanner, a retinal scanner, a DNA sensor, a microphone, or the like. The display may include, e.g., an LED array, an LCD, or the like. The actuators may include, e.g., a button, a toggle switch, or the like. The electronic ports may include, e.g., a USB port, a data port, a power supply port, or the like.

The BECDD device includes a communicator, such as, e.g., a radio frequency transceiver, that is configured to send and receive signals via, e.g., a cellular link, a GSM link, a WI-FI link, or the like, to notify and allow a patient to access an exact dose of the medication at a predetermined time as dictated by the physician.

The BECDD device is configured to receive pre-programmed messages, allowing precise medication doses at predetermined times. The BECDD device is also configured to send messages back to the DCMS. The BECDD device may send multiple messages, such as, e.g., verification: that the patient requested the medication upon notification; that the patient failed to request medication after receiving notification; the time and date at which the notification was received; that the medication was requested without notification; of an unauthorized biometric measurement a fingerprint scan); a copy of biometric information (e.g., a copy of the fingerprint); of battery life; a mechanical malfunction; a pill count; a tampering; a video file; a voice file; a receipt of remote programming instructions; and/or a GPS location. Additional messages can be programmed into the BECDD device.

According to a further aspect of the disclosure, a system is disclosed that includes at least one BECDD device, a DCMS, and a network. The BECDD device and DCMS may communicate directly or indirectly via, e.g., radio frequency (RF) links, infrared (IR) links, or the like.

The BECDD device may be loaded (or preloaded) with a BECDD computer program, which when executed on the BECDD device, will cause the BECDD device to perform the functions and processes described in the instant disclosure. The BECDD computer program may include a code section or segment for each process described in the instant disclosure.

The DCMS may be loaded (or preloaded) with a DCMS computer program, which when executed on the DCMS, will cause the DCMS to perform the functions and processes described in the instant disclosure.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

Figure 1:
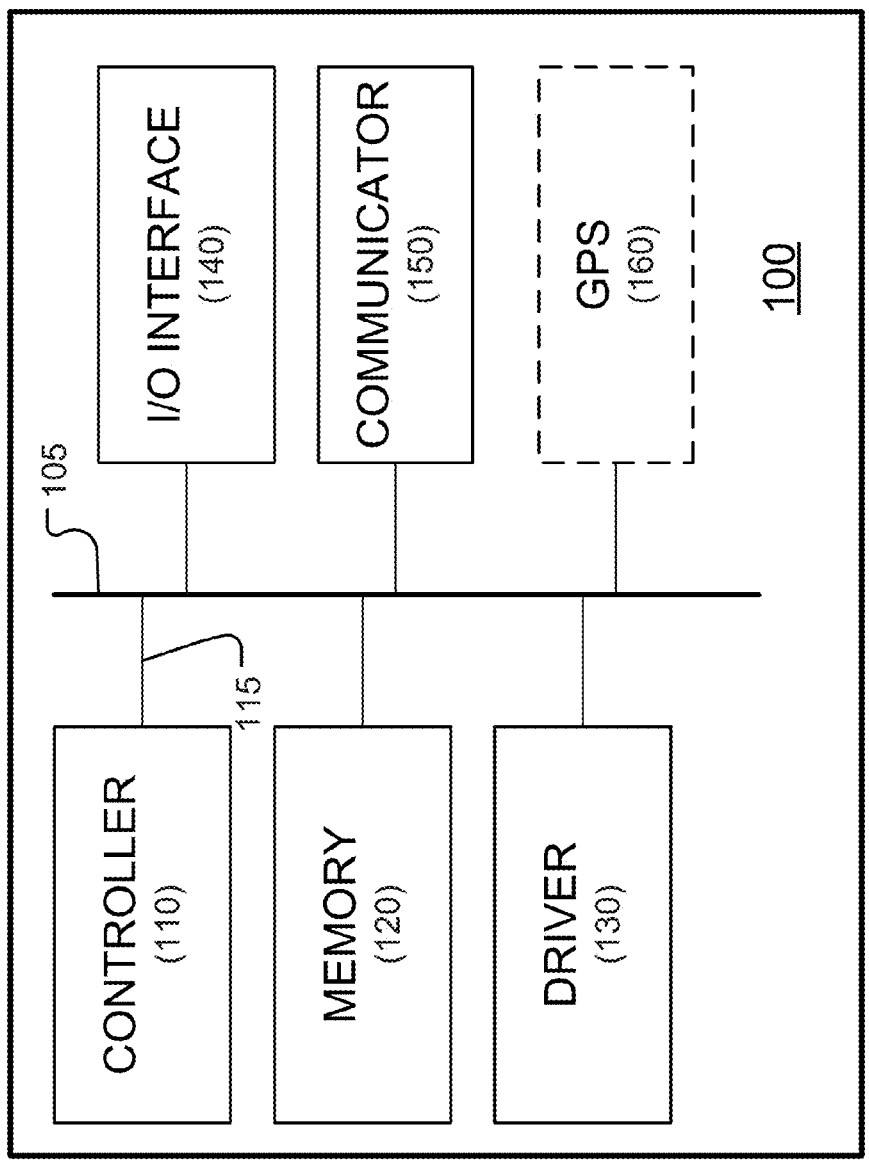
FIG. 1 shows an example of an electronic unit of a BECDD device that is constructed according to principles of the disclosure.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings and attachment are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

A "computer", as used in this disclosure, means any machine, device, circuit, component, or module, or any system of machines, devices, circuits, components, modules, or the like, which are capable of manipulating data according to one or more instructions, such as, for example, without limitation, ARM9 based microprocessor, a processor, a microprocessor, a central processing unit, a general purpose computer, a super computer, a personal computer, a laptop computer, a palmtop computer, a notebook computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "server", as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database", as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link", as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HTTP.

The terms "including", "comprising" and variations thereof as used in this disclosure, mean "including, but not limited to", unless expressly specific otherwise.

The terms "a", "an", and "the", as used in this disclosure, means "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

A "computer-readable medium", as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, tight waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

FIG. 1 shows an example of an electronic unit 100 that is constructed according to the principles of the disclosure. The electronic unit 100 comprises a controller 110, a memory 120, a drive 130, an input/output interface 140, and a communicator 150, each of which may be connected to a bus 105 via a communication link 115. The electronic unit 100 may further include a GPS receiver unit 160. The electronic unit 100 may also include an antenna (internal or external, not shown).

The electronic component 100 may be included in a BECDD device (e.g., BECDD device 200' shown in FIG. 7, or BECDDD device 450 shown in FIG. 9) and configured to communicate with like electronic components 100 that may be provided in other BECDD devices (not shown) and/or a DCMS (not shown). The electronic component 100 may include a computer readable medium that may inc hide a computer program that, when executed on a computer, can cause or facilitate in the carrying out of the steps shown in FIGS. 10-12. The computer program may be provided as a series of code sections or segments on the computer readable medium, each of which may be particularly configured to carry out one or more of the steps described herein, including the steps of the processes in FIGS. 10-12.

The electronic component 100 may reside on, e.g., a main printed circuit board (PCB), which may hold all of the major electronic components including the controller 110, the memory 120, the driver 130, the I/O interface 140, the communicator 150, and the GPS module 160. The PCB may be sized to fit in one side of the housing 200.

The power supply may be provided on the main PCB or a separate printed circuit board (PCB) to accomplish the needed power supply and hold the charging circuits (not shown). The separate PCB may be sized to fit, e.g., in the bottom side of the housing of the BECDD device and include multiple layers of PCB stacked, as is known in the art (e.g., 6 layers of PCB). The power supply may comprise one or more discrete DC/DC high efficiency modules and power supply ICs to provide all of the needed power requirements of the BECDD device. This may include, for example, 1.2V, 1.8V, 2.5V, 3.3V, 5V, and the like. All components may be selected to maximize battery life and minimize discharge rates.

The power supply module may contain an inductive battery charger circuit (not shown) to recharge the battery pack as needed. This may be accomplished by placing the BECDD device onto a charging pad thereby receiving charging power via inductive coupling without the use of wires or physical connections between the two systems. The selected chipset allows for smart charging to maintain efficiencies and safety.

In order to support traveling, the BECDD device may include, e.g., a Li-ion battery pack sized to run the device for one or more days.

The controller 110 may include a computer. The controller 110 is configured to receive inputs from the various authentication sensors in the BECDD device, including, e.g., an optional camera, a fingerprint reader, a photo detector, a blood sample extractor, a DNA sample extractor, and the like. The controller 110 is further configured to receive inputs from user interface devices, including, e.g., switches, buttons, touch-sensors, and the like. The controller 110 is further configured to run operating software and/or firmware and make decisions on which action to take. The controller 110 may exchange data signals, including control signals, with the various components in the BECDD device, including, e.g., the biometric sensor(s), the camera, an indicator (e.g., a tight strobe, an audible indicator, or the like), the display, the actuators, the memory 120, the driver 130, the I/O interface 140, the communicator 150, the GPS module 160, and the like.

The input/output interface 140 may include, e.g., a display, a display driver, a speaker, an audio driver, a microphone, an optical scanner, a touchpad, a keypad, a mouse, a fingerprint scanner, an optical scanner, a video camera, or the like. The driver 130 may include hardware and/or software to actuate, drive, and control a mechanical component (not shown) that dispenses medication from a BECDD device BECDD device 200' shown in FIG. 7). The driver 130 may also be configured to drive a locking mechanism (not shown) that engages and holds a drug cartridge (e.g., drug cartridge 240' shown in FIG. 7) in the BECDD device housing. The driver 130 may be integrated into the BECDD device together with a motor (not shown). The driver 130 is configured to receive instructions from the controller 110 and to generate motor drive signals based on the received instructions. The motor (not shown) may be configured to actuate a dispensing mechanism (not shown) for pill dispensing. The controller 110 may receive feedback signals from the driver 130 and/or the motor (not shown) for precise control.

The display may include, e.g., an OLED display (e.g., 128×64), which may provide feedback to, e.g., a pharmacist during setup and programming. For the caregiver and patient, the display may provide information at the time of dispensing and also indicate the BECDD device's status.

The video camera (e.g., 640×480) may provide a video/picture of the user accessing the BECDD device for dispensing of medication. The camera may also validate cartridge replacement or document unauthorized access. The captured images (e.g., JPG/MPEG images) may be sent out to a DCMS (not shown).

The fingerprint reader may be configured to take an initial scan of the user's fingerprint (e.g., care giver, patient, or the like) and store the fingerprint data in the memory 120 for control access. In the case of a caregiver, the fingerprint reader may allow access to replace the cartridge and dispense medication as programmed. Additionally, a patient may be given rights to scan his finger and receive medication directly.

The BECDD device may include a photo sensor to validate the dispensing of an individual pill by the device.

The communicator 150 and the UPS module 160 may be utilized to attain several design goals, including back and forth communication with the DCMS. This communication may include messages about pill dispense status, an (optional) photo image of the user utilizing the unit for verification purposes, new commands or firmware updates, and the like. The UPS module 160 may receive satellite signals to provide location information of the BECDD device. This UPS location may be used in conjunction with the programmed location by, e.g., the pharmacy to implement an electronic GEO fence around the BECDD device which may allow the DCMS to know if the BECDD device is removed from its intended location of use. This could also be initiated by an incorrect fingerprint read. This would aide in the tracking of the BECDD device if it was stolen.

The BECDD device may include one or more internal antennas for the communicator 160 and UPS module 160. In conjunction with these antenna designs, appropriate shielding may be included, surrounding the electronics to avoid RF interference and appropriate pre-testing may be done to validate the antenna's designs. By utilizing internal antennas, the unit may remain streamlined and more rugged.

The BECDD device may include firmware, which may be developed in, e.g., Linux, which may be run by the controller 110. The firmware may include, e.g., the following modules: a main module, a time module, a video capture module, a fingerprint capture module, a dispense action module, a communication module, a GPS module, and a firmware updates module.

The main module may include mainline run routines that will oversee the operation of the BECDD device. This module may receive inputs from other modules and make decisions that may be output to other modules. This module may coordinate all of the activities of the device.

The time module may be responsible for keeping track of the time for dispensing and other activities to occur. In simple terms, it may act as an alarm clock for the BECDD device.

The video capture module may setup the optional hardware camera module to initiate a picture on demand. The module may also prepare the raw video picture to a JPEG file format, ready for transmission to the DCMS.

The fingerprint capture module may initialize the fingerprint reader and inquire if the module has received a valid/invalid fingerprint read. The response may be communicated to the DCMS.

The dispense action module may control the aspects of the dispensing mechanism. It may be responsible for driving the motor and sensing feedback during the dispense cycle.

The communication module may control sending and receiving data for the BECDD device. The communication module may receive data from the main module, which may receive inputs from the various other modules. The communication module may coordinate and control transmission (or reception) of data between the BECDD device and DCMS, as well as other BECDD devices. Firmware updates may be received through the communication module.

The GPS module may take the task of updating the BECDD device with GPS coordinates and help implement a GEO fence around the device by comparing the received GPS to the programmed address from, e.g., the pharmacy. Triggers such as an incorrect fingerprint read could initiate the GEO fence to start logging.

The firmware updates module may periodically check the DCMS for firmware updates. The module may also check the DCMS for firmware updates every time the BECDD device is returned to, e.g., the pharmacy for reloading the firmware.

Figure 2:
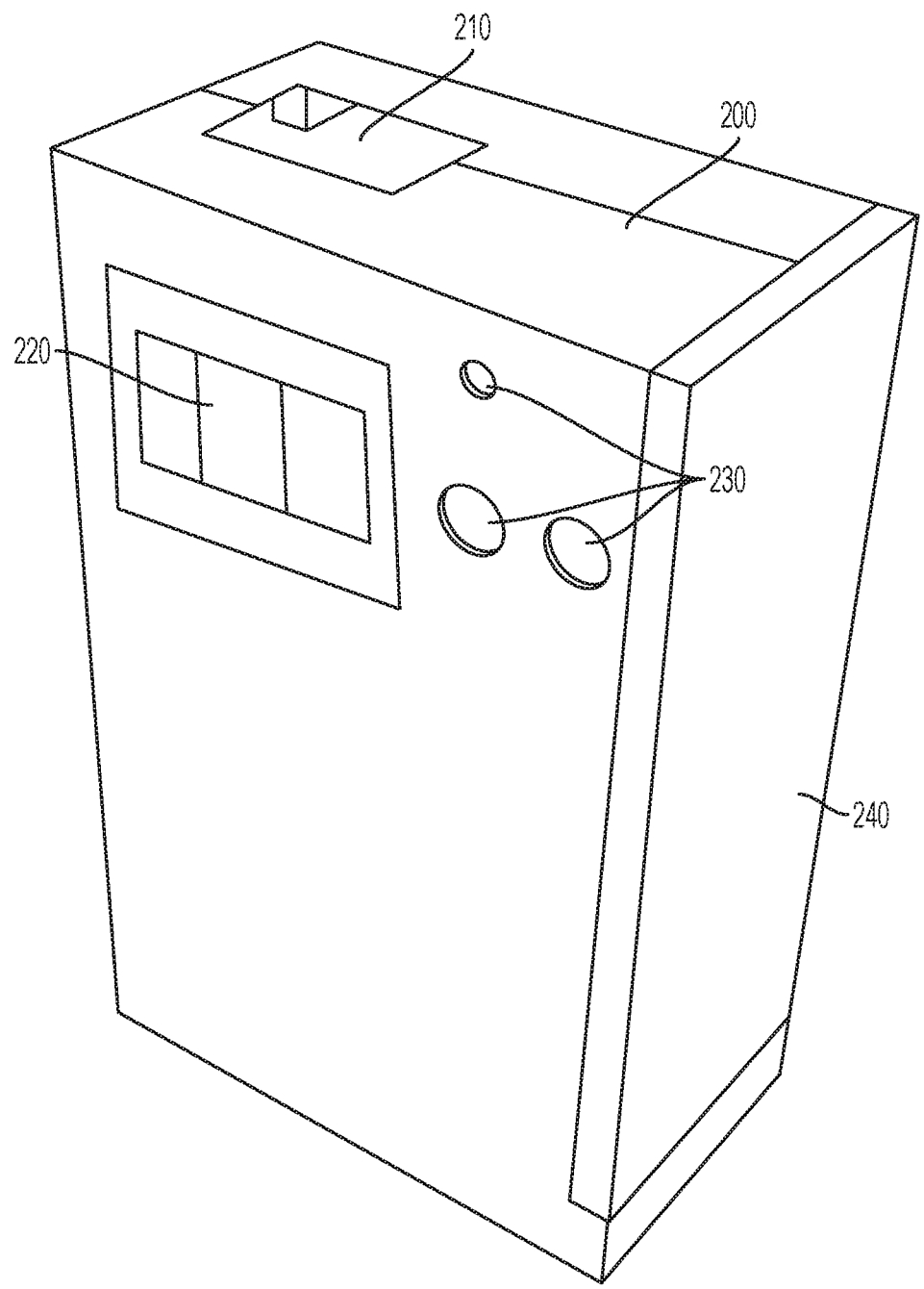
FIG. 2 shows a perspective view of an example of a housing for a BECDD device that is constructed according to the principles of the disclosure.
Figure 3:
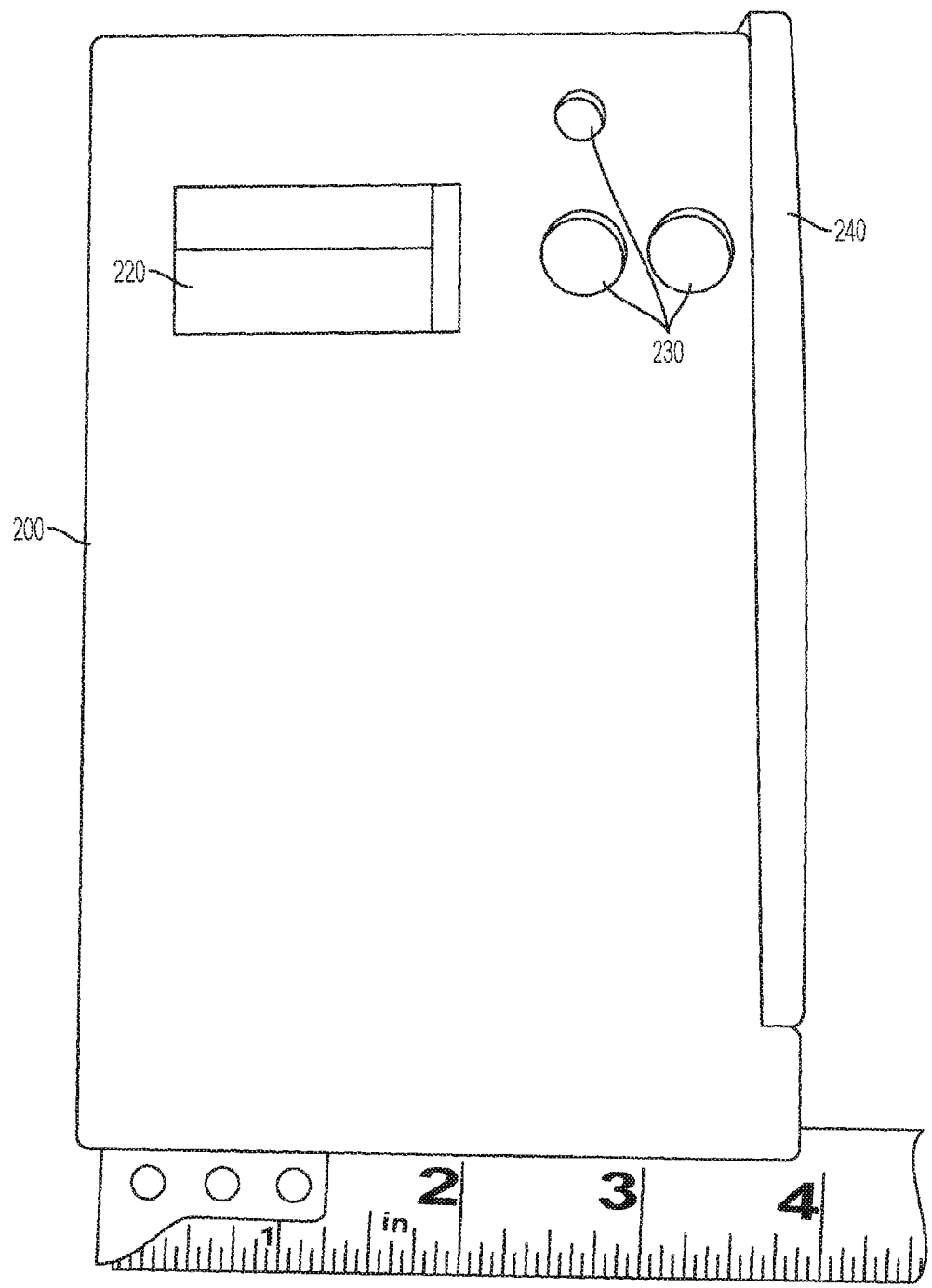
FIG. 3 shows a front view of the housing of FIG. 2.
Figure 4:
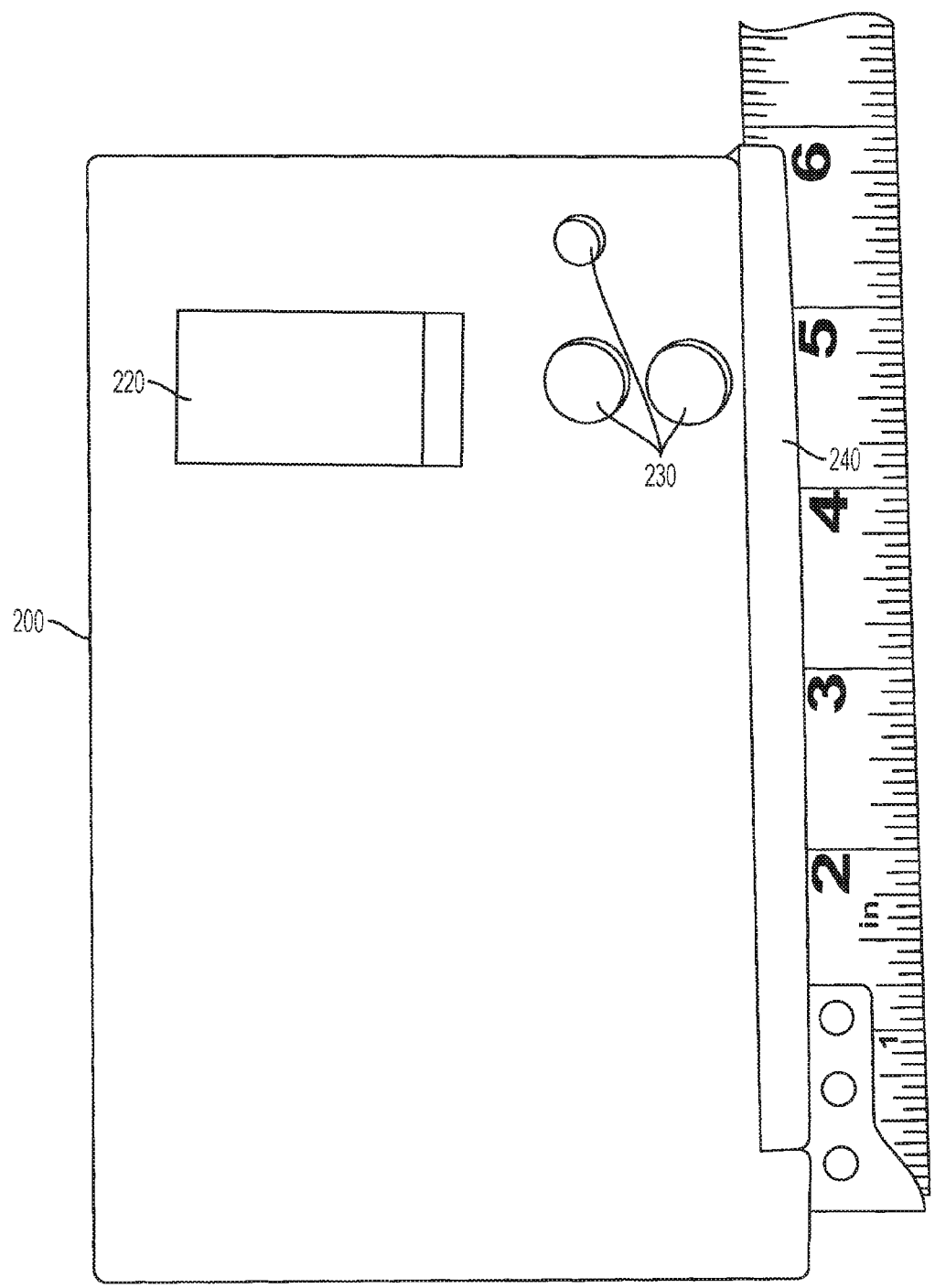
FIG. 4 shows another front view of the housing of FIG. 2.
Figure 5:
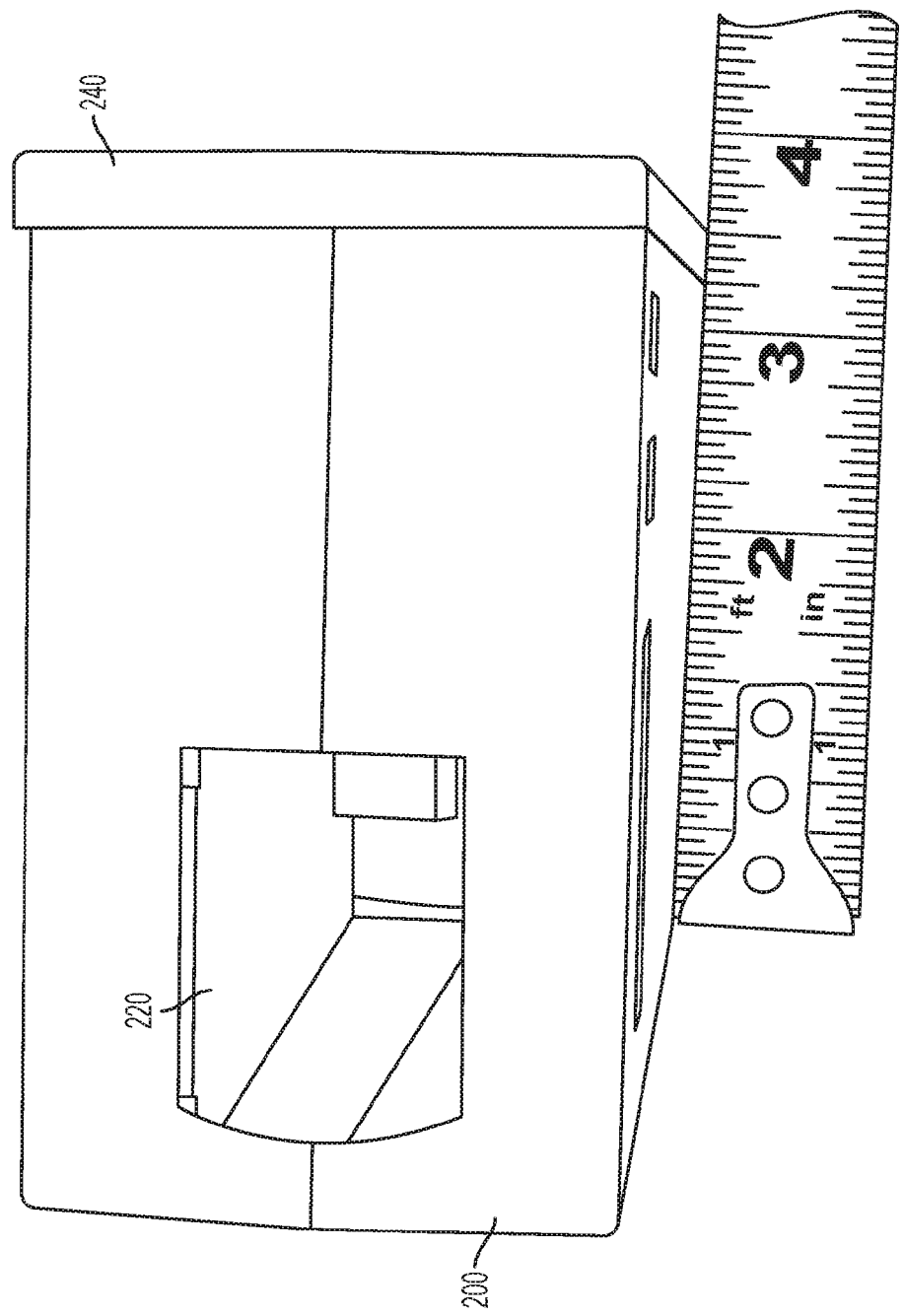
FIG. 5 shows a top view of the housing of FIG. 2.
Figure 6:
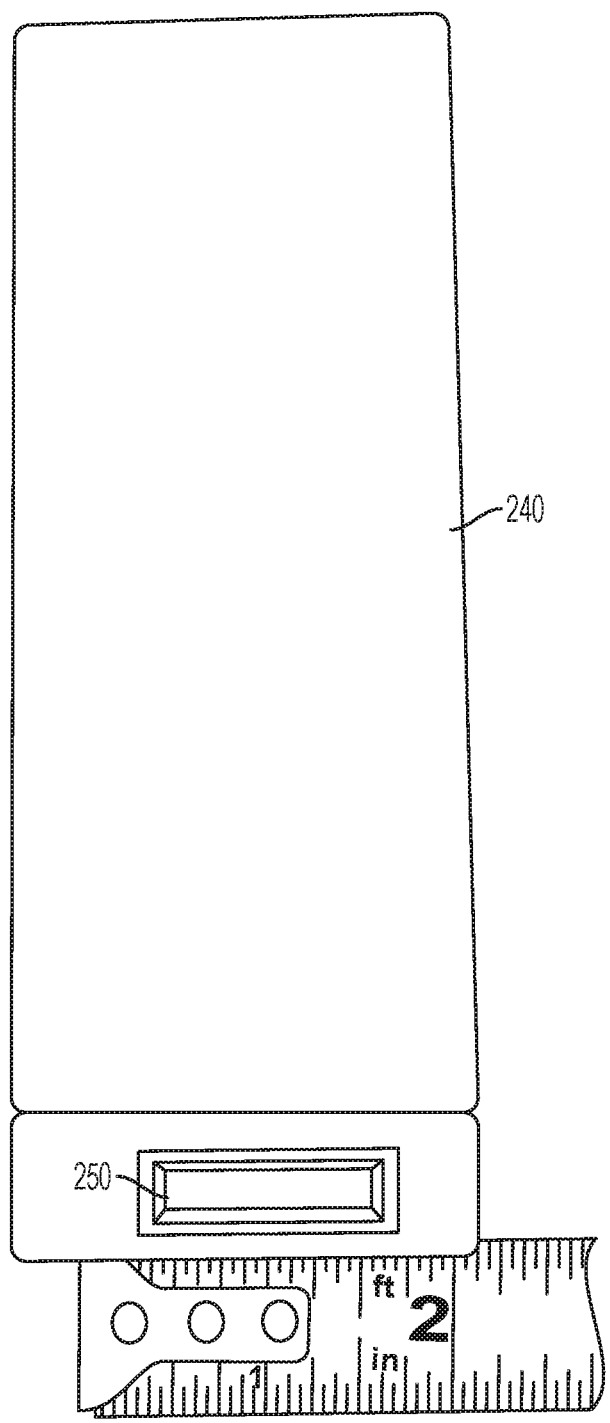
FIG. 6 shows a dispenser side view of the housing of FIG. 2.

FIGS. 2-6 show various views of a housing 200 for a BECDD device that is constructed according to the principles of the disclosure. In particular, FIG. 2 shows a perspective view of the housing 200; FIG. 3 shows a front view of the housing 200; FIG. 4 shows another front view of the housing 200; FIG. 5 shows a top view of the housing 200; and FIG. 6 shows a dispenser side view of the housing 200. Referring to FIGS. 2-6, the housing 200 comprises a biometric sensor opening 210, a display opening 220, a plurality of actuator openings 230, a drug cartridge 240, and a dispensing opening 250.

The drug cartridge 240 provides a means for single dose pill dispensing. The cartridge 240 supports easy access load and reload capability for authorized provisioning users, such as, e.g., pharmacy personnel. The drug cartridge 240 may include, e.g., a spring-loaded magazine (not shown) that receives, holds, and stages pills for dispensing. The spring tension may be selected to provide adequate force to mechanically stage each pill in the drug cartridge 240 for dispensing from the BECDD device 200' (300). The spring-loaded magazine may be configured to hold a series of pills, one-a-top the other in substantially a single plane or one-a-top the other, with each pill being offset from an adjacent pill, similar to, e.g., an ammunition magazine that may be used in, e.g., a semi-automatic firearms, which may include a series of linearly stacked ammunition rounds or a series of off-set linearly stacked ammunition rounds to provide for a more compact, high capacity cartridge. The BECDD device 200' (300) may include a sensor (e.g., a photo sensor) to detect a pill as it is dispensed from the drug cartridge 240 (or 340), including as the pill exits into a guide tube (not shown) and proceeds toward the tray 360 (shown in FIG. 8).

Figure 7:
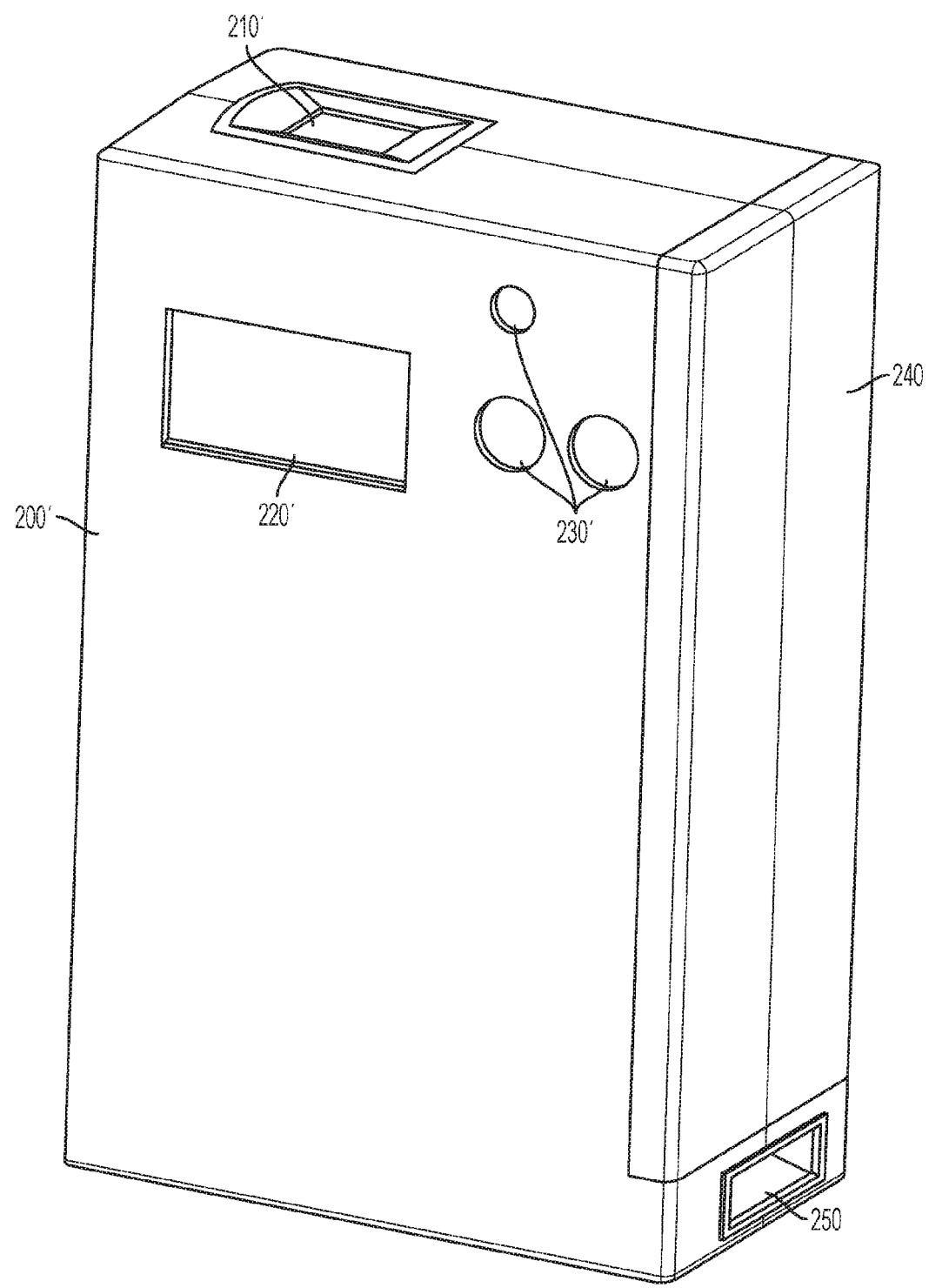
FIG. 7 shows a perspective view of an example of a BECDD device that is constructed according to the principles of the disclosure.

FIG. 7 shows a perspective view of a BECDD device 200' that is constructed according to the principles of the disclosure. The BECDD device 200' comprises a fingerprint scanner 210', a display 220', one or more actuators 230', the drug cartridge 240, and the dispensing opening 250, The BECDD device 200' may also include a microphone, a camera, a speaker, or the like.

Figure 8:
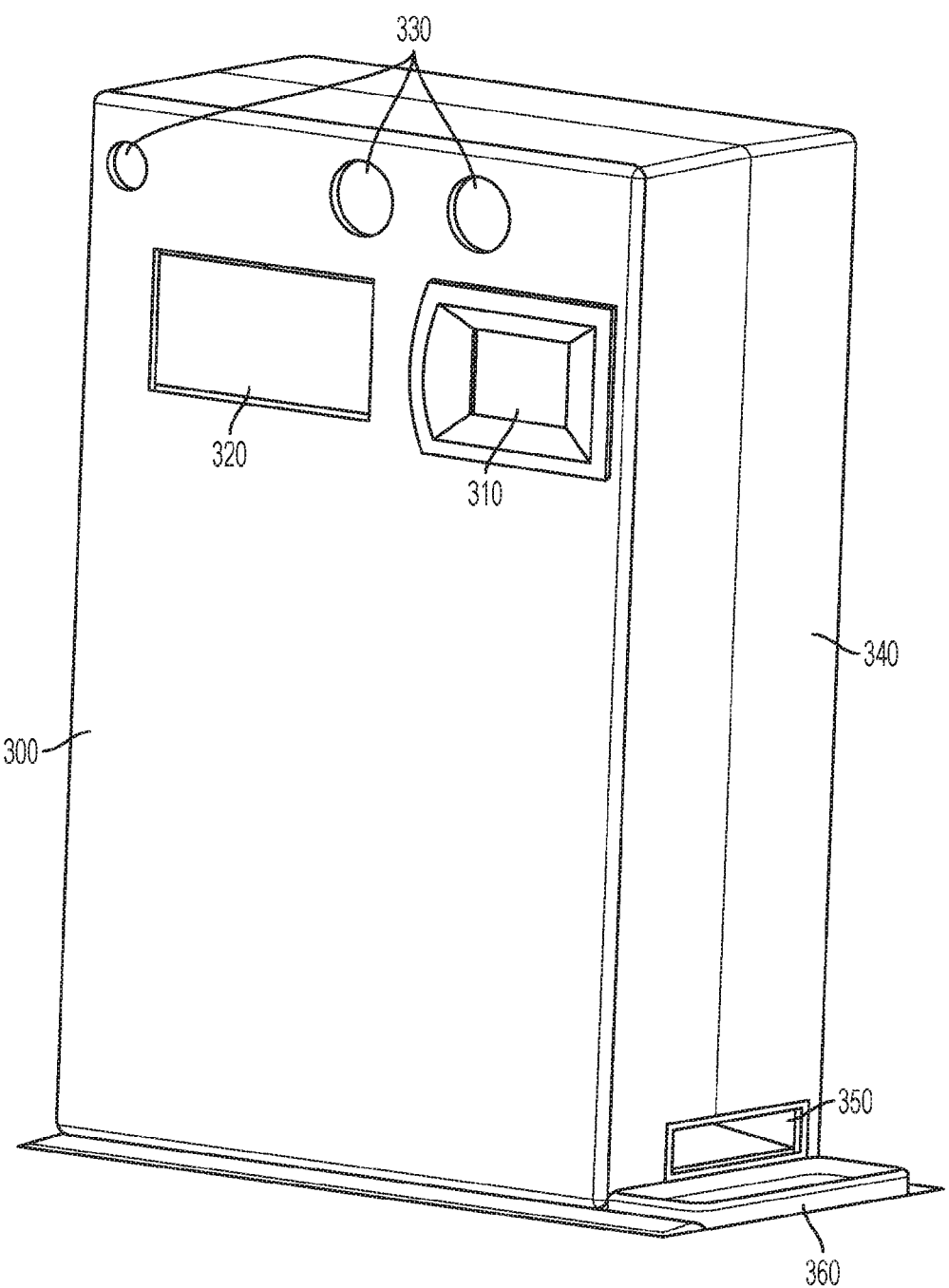
FIG. 8 shows a perspective view of another example of a BECDD device that is constructed according to the principles of the disclosure.

FIG. 8 shows a perspective view of a BECDD device 300 that is constructed according to the principles of the disclosure. The BECDD device 300 comprises a fingerprint scanner 310, a display 320, one or more actuators 330, a drug cartridge 340, a dispensing opening 350, and a dispensing tray 360.

The BECDD device 200' (300, 450) may be configured to sit on a charging station (not shown).

The BECDD device 200' (300, 450) is a portable unit that controls the dispensing of a pill from the installed cartridge 240 (340). In order to get a pill from the BECDD 200', the user may place his index finger in the correct position on the built-in finger print reader 210' (310), The BECDD device 200' authorizes the transaction based on the provisioning of the device by an authorized provisioning user, such as, for example, a caregiver, a pharmacist, a prescribing physician, or the like. The authorization functions may be transparent to the end user unless an exception occurs. The BECDD device 200' may report exceptions in the form of exceptions data (such as, e.g., an indication of a failure to take medication, an indication of an attempt to take medication too frequently, an indication of a tamper attempt, etc., a time-stamp (e.g., date and time) of each of the foregoing events, identification data of the person attempting to access the medication, etc.) upon generation of the event back to a remote device, the DCMS (not shown). The reported exceptions data may include, e.g., identification data that may be used to identify the person trying to access the medication, such as, e.g., a fingerprint, a photo, a voice signature, a retina image, or the like. The reported exceptions data may be stored at the DCMS and associated with the particular user and/or BECDD device. The exceptions data may be forwarded (e.g., by the DCMS and/or the BECDD) to, e.g., the user's physician.

Exceptions and possible corrective actions may be reported to the user locally on a display 220' (320). Exceptions and possible corrective actions may also be reported to, e.g., the user's physician, or other predetermined individual(s). Events that are not considered exceptions may also be reported back to the DCMS at the discretion of the operator of the DCMS. The BECDD 200' is capable of being relocated without loss of service, and without requiring special actions by the end user, Power to the BECDD 200' may be provided by a wall mount power supply and backed up by a rechargeable battery.

According to an aspect of the disclosure, the BECDD may be configured so that the DCMS can control operations of the BECDD remotely, including, e.g., dispensing, powering down, powering up, displaying a message, generating a sound, vibrating, and the like. Accordingly, upon identification of an exceptions event, the DCMS may send a signal to the BECDD to display a message, generate a sound, vibrate, or the like, so as to communicate a desired message to the user or individual handling the BECDD.

For instance, if a user misses a scheduled dosage, exceptions data may be generated and sent to the DCMS. The DCMS may instruct the BECDD to sound an alarm, display a message, and/or vibrate, thereby alerting the user and reminding the user to take a scheduled dosage. The DCMS may also generate and send a message to, e.g., the user's physician, informing the physician that the user has missed a scheduled dosage. The message may be communicated via, e.g., email, telephone, SMS text messaging, or the like.

If a user requests a dosage prior to a scheduled time, exceptions data may be generated and sent to the DCMS. The exceptions data may be associated with the user personal data and/or BECDD at the DCMS and stored for later access. The exceptions data may include the identification data for the person attempting to access the medication.

The BECDD 200' may have two operational phases, including a pharmacy loading phase and a pill dispense phase.

The BECDD device 200 (200', 300, or 450) may be configured to capture audio by means of a microphone (e.g., microphone in I/O interface 140, shown in FIG. 1), so that a user may activate an actuator (e.g., press a record button) that instructs the BECDD to record a message from the user, which may include, e.g., a summary of side-effects potentially related to the medication being (or that has been) dispensed by the BECDD to the user. The recorded message may be sent automatically to the DCMS (e.g., DCMS 410, shown in FIG. 9), where the message may be stored in a record associated with the particular user and/or BECDD device. Further, the message may be transcribed and a transcription of the message stored in the DCMS.

The BECDD may be configured to store data and control signals that are intended to be communicated to the DCMS, even when the communication links 405 are inactive or inaccessible, so that when a communication link is established between the BECDD and the DCMS, the data and/or control signals may be communicated at a delayed time (non-real-time).

Figure 9:
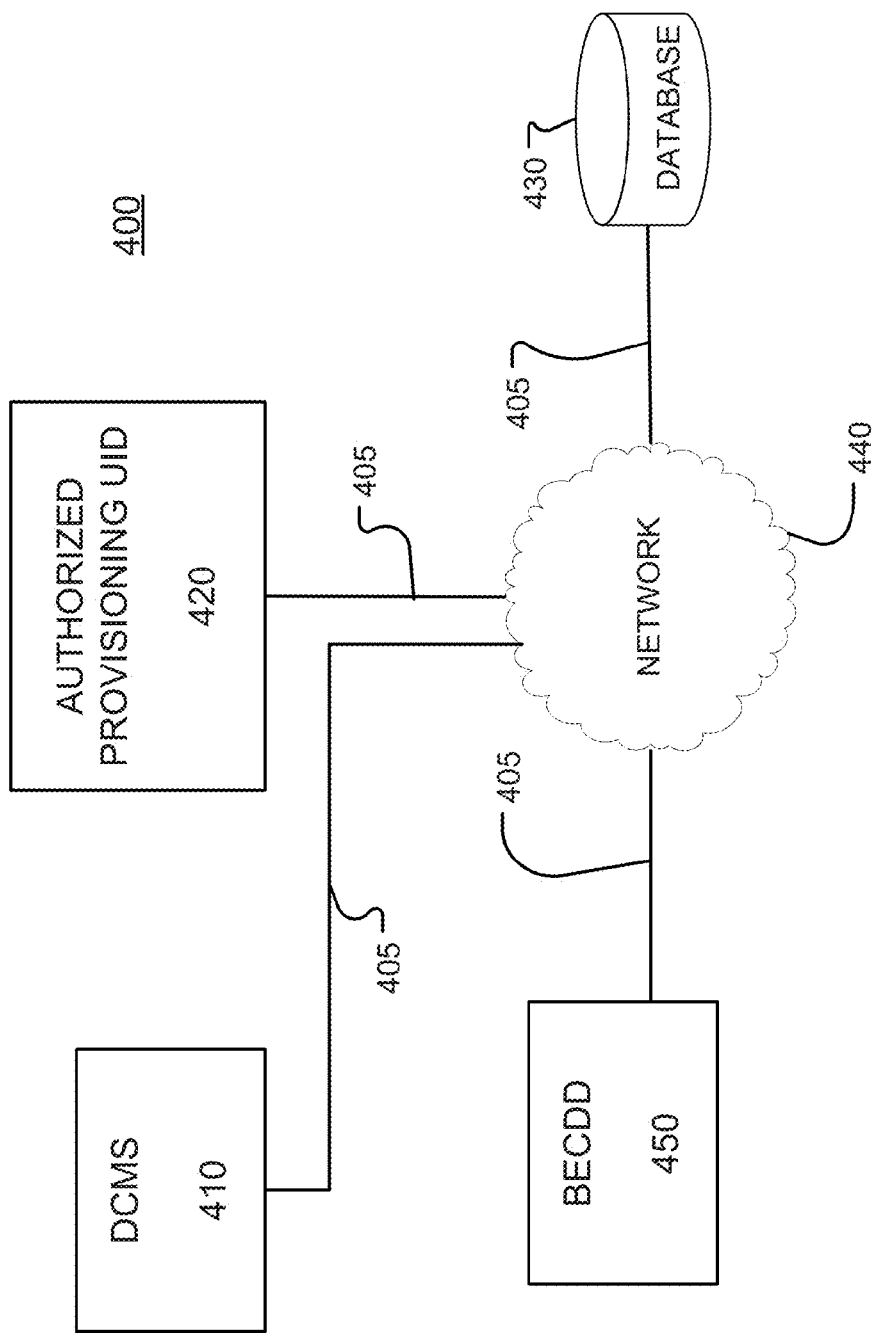
FIG. 9 shows an example of a BECDD dispensing system that is configured, according to the principles of the disclosure.

FIG. 9 shows an example of a BECDD dispensing system 400. The BECDD dispensing system includes the DCMS 410, an authorized provisioning user interface device (UID) 420, a database 430, a network 440, and a BECDD 450, all of which may be connected to each other directly and/or through the network 440 via one or more communication links 405. The DCMS 410 may include a server. The authorized provisioning UID 420 may include a computer. The BECDD 450 may be substantially the same as, for example, the BECDD device 200, 200', or 300.

Figure 10:
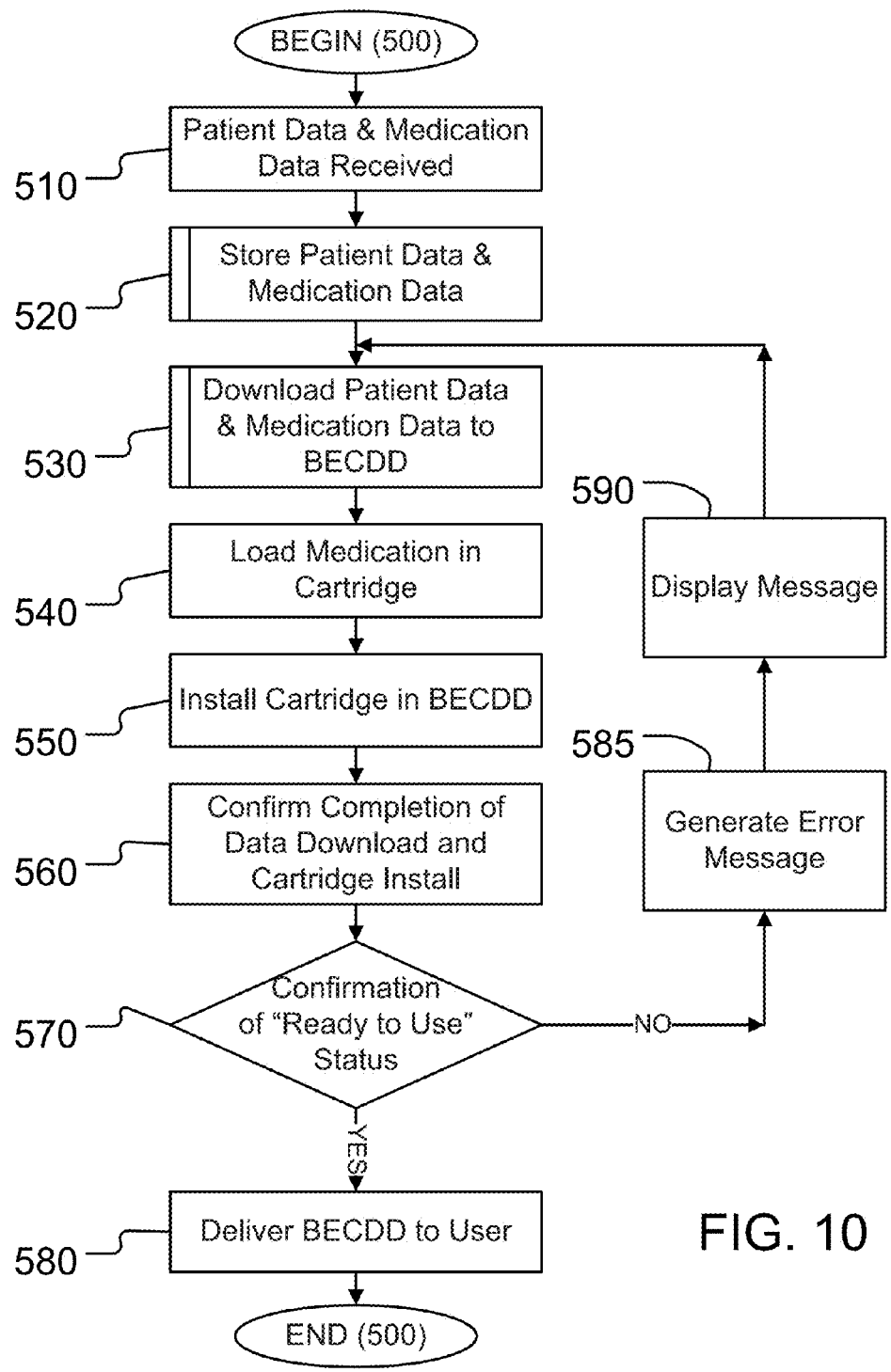
FIG. 10 shows an example of a pharmacy loading phase (PLP) process, according to the principles of the disclosure.

FIG. 10 shows an example of a pharmacy loading phase (PLP) process 500, according to the principles of the disclosure. The PLP process 500 includes a plurality of steps that may take place when loading, e.g., the BECDD device cartridge 240 (or 340) and configuring the BECDD 450 for use by the user.

Referring to FIGS. 9 and 10, after the PLP process 500 begins, patient data and medication data may be received from, e.g., an authorized provisioning user (e.g., a pharmacist) (Step 510). The patient data may include, for example, a name, an age, a birth date, an address (e.g., street address, email address, GPS coordinates, or the like), a telephone number, a social security number, allergy information, medical history, a finger print, a retina image, DNA, a face photo, a foot print, or the like. The medication data may include, for example, a brand name, a dosage amount, a dispensing schedule, an expiration date, a list of ingredients, a list of active ingredients, and the like. The patient data and the medication data may be received by the DCMS 410 (shown in FIG. 9) from, e.g., the authorized provisioning UID 420 via the communication link 405. The patient data and medication data may be stored locally at the DCMS 410 (e.g., in a server) and/or the database 430, which may be located locally at the DCMS 420, or remote from the DCMS 420 (Step 520).

The patient data and medication data, or certain subsets of the patient data and medication data may be downloaded from the DCMS 420 to the BECDD 450 (Step 530) via the communication links 405.

Medication may be loaded, e.g., by the authorized provisioning user (e.g., pharmacist) into the cartridge (e.g., cartridge 240) (Step 540). The loaded cartridge may then be installed in the BECDD 450 (Step 550). The BECDD 450 may communicate with the DCMS 410 to confirm completion of the proper loading of the personal data and medication data in the BECDD 450 and proper installation of the cartridge in the BECDD 450 (Step 560). After a determination is made that the personal data and medication data have been downloaded and the cartridge properly installed in the BECDD (YES at Step 570), the ready to use BECDD may be provided to the user (Step 580).

If, however, a determination is made that the BECDD 450 is not ready to use, e.g., because the necessary personal data and/or medication data has not been loaded in the BECDD 450, or the cartridge is not properly installed in the BECDD 450 (NO at Step 570), a message may be generated and sent to the BECDD 450 and/or the authorized provisioning UM 420 (Step 585). The message may be displayed on the BECDD 450 (and/or the authorized provisioning LID 420), informing the provisioning user that the BECDD 450 is not ready for use, and providing an error message (e.g., an error code, a written message, a spoken message, or the like) that informs the provisioning user on the cause of the error (Step 590). The message may also include steps that may be taken to correct the error status and place the BECDD 450 in ready-to-use condition, including re-downloading patient data and medication data to the BECDD 450 and repeating the installation steps (Steps 530 to 570).

Figure 11:
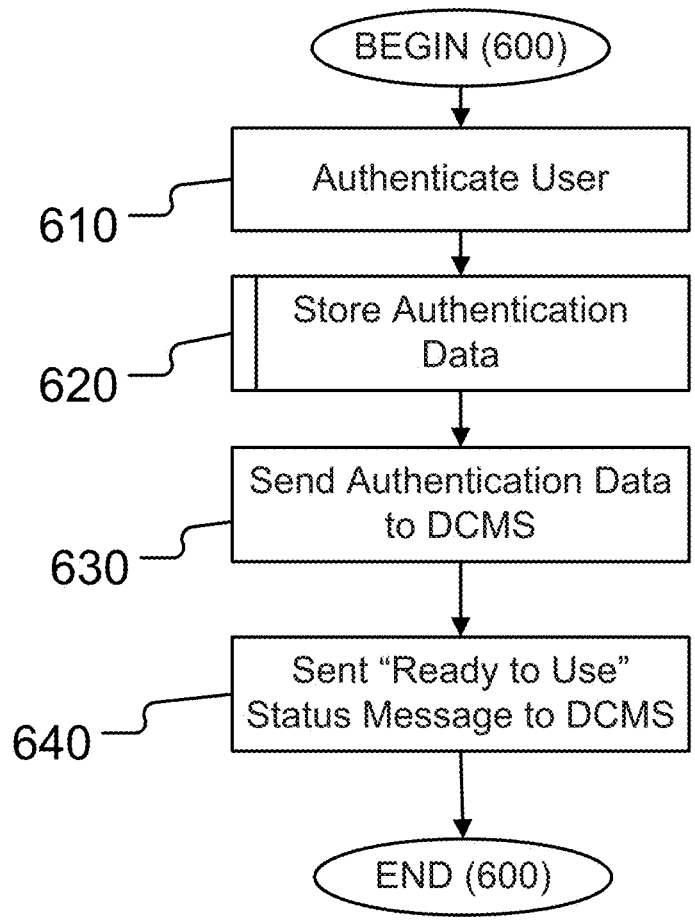
FIG. 11 shows an example of a pill dispense initialization phase (PDI) process, according to the principles of the disclosure.

FIG. 11 shows an example of a pill dispense initialization phase (PDI) process 600, according to the principles of the disclosure. The PDI process 600 may include a plurality of steps that may take place when dispensing a drug by a user.

Referring to FIGS. 9 and 11, after the ready to use BECDD 450 is delivered to user (Step 580, FIG. 10), PDI process 600 may begin. Since the BECDD 450 is configured for a particular user, the user may be authenticated (Step 610) by receiving user authentication data. The user authentication data may include, biometric information (such as, e.g., retina image, face image, fingerprint, DNA sample, blood sample, etc.), voice signature, and the like. For instance, user authentication data that includes finger print data may be received by having the user (e.g., patient) place his/her finger on the fingerprint reader 210' (310).

The authentication data (e.g., finger print) may be stored in a local memory (e.g., the memory 120, shown in FIG. 1) of the BECDD 450 (Step 620). The authentication data may be sent by the BECDD 450 to the DCMS 410 (Step 630). After the authentication data has be stored in the BECDD, the BECDD may notify the DCMS 410 of a ready to dispense status (Step 640).

The initial dose interval may be initiated by either or both the BECDD device 200' or the DCMS.

The BECDD 450 may be configured to carry out a pill dispense sequence phase (PDSP) process 700. The PDSP process 700 may be controlled by, e.g., the controller 110 (shown in FIG. 1) in the BECDD.

Figure 12:
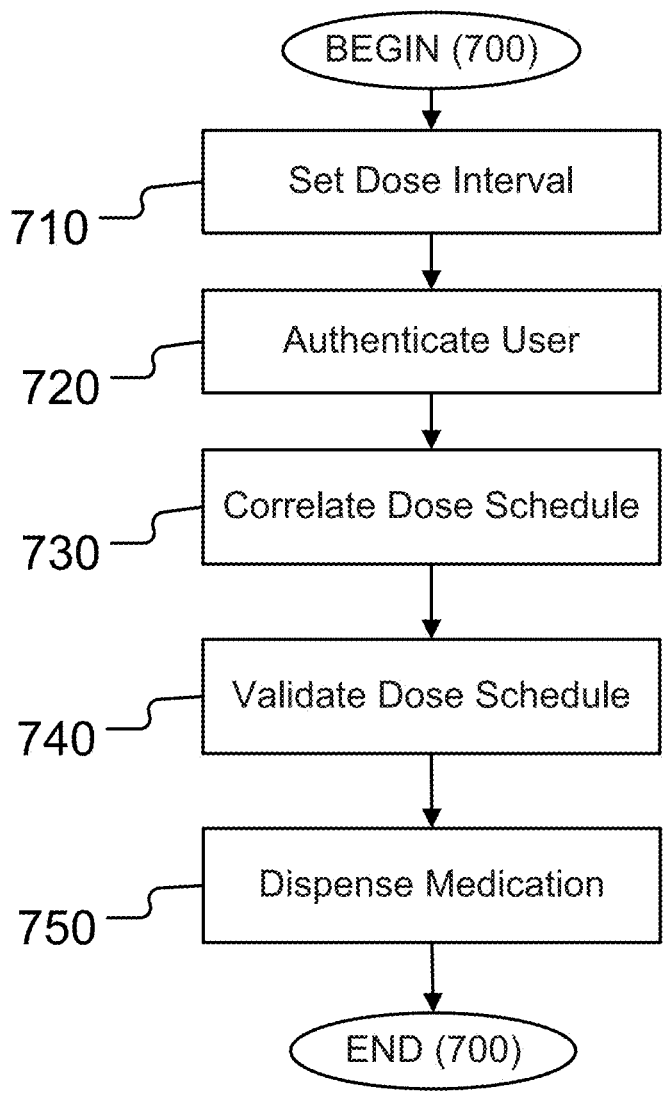
FIG. 12 shows an example of a pill dispense sequence phase (PDSP) process, according to the principles of the disclosure.

Referring to FIG. 12, the PDSP process 700 may include setting a dose interval with audio and/or visual alerts (Step 710); performing a user authentication (e.g., a fingerprint scan) (Step 720); correlating a dose schedule with a dose schedule stored at a DCMS 410 (Step 730); validating the dose schedule (Step 740); and dispensing a medication dosage from the BECDD 450 (Step 750). The user (e.g., patient) may then take the dispensed medication. After completion of the PDSP process 700, the BECDD 450 may return to the dose delivery schedule for the next dispensing event.

Referring to FIGS. 2-8, the BECDD device 200' (300) includes the housing 200, which may be configured to sit on a charging station (not shown). As seen the BECDD 200' (300) may include a display 220', a finger print reader 210', a camera (optional, not shown), and a medication arresting tray 360 for pill capture during the dispense cycle. The display 220' may support, e.g., pharmacy programming, as well as a patient and or a caregiver interface. The finger print reader 210' may be used for patient identification/validation.

The housing 200 may be provided with a keyed door (not shown) for limited access to load/reload the medication cartridge 240. The BECDD 200' (300) may be programmed via, e.g., a USB port, a GSM SIM card, a wireless link, or the like. The keyed door may be mechanically (and/or electronically) locked. The USB port may also be used as an alternate means to charge the battery.

The keyed door may be mechanically locked, e.g., with a spring loaded lock that has a pinhole lock de-activation mechanism (not shown). The door may be configured to conceal and limit access to, e.g., the USB connection, the GSM SIM card, and the like. The door may be further configured to limit access to the medication cartridge 240. An authorized entity such as, e.g., a pharmacy, a clinic, a physician, or the like, may be provided with a key (mechanical or electronic) to unlock the door.

In the case of a mechanical door, a pinhole mechanical lock may be used, which provides a secure, low cost, simple mechanical locking mechanism. The intent is to provide an inconspicuous lockout to the access door of the BECDD device 200' (300). For example, a spring-loaded access door lock may include a pinhole for a wire key, which will allow access to inner portions of the housing of the BECDD device 200' (300).

As noted earlier, the BECDD device 200' (300) may be equipped with an optional camera that could be used to validate that the patient is taking the medication at the scheduled time intervals. The camera may be also used for patient identification, as well as for theft identification.

The BECDD device 200' (300) may include a motor (not shown) to actuate, extract, and dispense medications from the medication cartridge 240 (340) of the BECDD device 200' (300). The motor may be controlled by, e.g., the driver 130 (shown in FIG. 1), The BECDD device 200' (300) may further include a guide mechanism (not shown) that mechanically (or electrically) orients the drug cartridge 240 (340) in the housing of the BECDD device 200' (300). The BECDD device 200' (300) may be configured to receive various sizes and/or shapes of drug cartridges 240 (340). The drug cartridge 240 (340) may be configured to receive and hold, e.g., pills that are about 6.4 mm to about 22 mm in size. The drug cartridge 240 (340) may be configured to receive and hold other sizes of pills. It is noted that throughout this disclosure, the terms "pill", "medication", and "drug" have been used interchangeably.

The BECDD device 200' (300) may further include a GPS module (e.g., GPS module 160, shown in FIG. 1), which may provide geographical coordinates of the BECDD device 200' (300) in real-time. These coordinates may be communicated to, e.g., the DCMS via, e.g., the communicator 150 (shown in FIG. 1).

The BECDD device 200' (300) is constructed for use in standard human habitat. The BECDD device 200' (300), including all components, is further constructed to be stored and to operate from about 0° F. to about 120° F. (−18° C. to 49° C.). Other temperature tolerances are contemplated for the BECDD device 200' (300), including temperatures greater than 120° F. and/or less than 0° F. The temperature range allowed by the cartridge 240 (340) contents may reduce this temperature range as necessary. If temperature range reduction is necessary, the cartridge 240 (340) may indicate so on a printed stick-on label. If printed on a tamper evident seal, the seal may perform the notification function.

The BECDD device 200' (300) may be constructed from materials that are known to be non-toxic to humans and non-reactive with the contents to be included in the drug cartridge 240 (340). The exterior of the BECDD device 200' (300) may include four parts, including: a main base that has a left side and a right side; a front face that conceals a seam and fasteners, which hold the main base sides together, and houses the finger print reader 210' (310), video camera (not shown), and display 220' (320), The BECDD device 200' (300) may include an access door that will limit access to the medication cartridge slot (not shown), USB port, GSM SIM card, and the like. The finger print reader 210' (310) may be positioned on the front face or on the top of the BECDD device 200' (300), so that is easy to reach. The display 220' (320) may be angled, top mounted or side mounted to allow reading during programming and pill dispense or patient use. The video camera may be located on the front, top or side of the BECDD device 200' (300).

The instant system, device, method, and computer program provide a solution for, e.g., non-compliant patients, medication errors, prescription medication abuse, medication thefts, and inaccurate reporting. Transplant patients, drug study patients, elderly patients, non-compliant patients, Alzheimer patients, clinics, physicians, may be provided with a BECDDD device that notifies the patient when it is time for their medication, and at the same time generate a record of the event. The BECDD device may prevent and/or reduce prescription drug abuse, unauthorized access to patient medications, theft, accidental overdose, forgotten dose, and increase patient compliance. Care providers may know in minutes that a patient has or has not taken or requested medication.

The BECDD device may save hospitals, clinics, drug companies, and the like an incredible sum of money, while reducing medication errors. Only the patient's biometric information can activate the drug dispenser. The exact drug at the exact time may be administered. The patient cannot accidentally take too many or the wrong medication. The BECDD device provides accurate and timely reporting for drug companies conducting drug studies/trials attempting to take a new drug to market. The BECDD device may track patient activity and notify a clinic immediately if the patient becomes non-compliant. Tire device also allows care providers access to instant reporting of compliant or non-compliant patient medication use. Care Providers may know in substantial real-time (e.g., in seconds or minutes), not hours, days, weeks or even months that a patient has not been taking their medication.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed:

1. A biometric electronic communicating drug dispenser (BECDD) device, comprising:
    an authentication sensor including a camera that senses authentication attributes of a user and generates a user authentication signal;
    a controller that receives the user authentication signal from the authentication sensor and generates a dosage dispensing instruction based on a dosage schedule at a remote computer; and
    a medication dispenser that dispenses a dosage under control of the controller based on the dosage schedule to control access to the dosage by the user,
    wherein the medication dispenser comprises an actuator that receives the dosage dispensing instruction from the controller and is configured to dispense the dosage,
    wherein the BECDD device further comprises a generally rectangular shaped housing that receives the medication dispenser having a generally rectangular shape, the medication dispenser comprising a spring-loaded dispenser that holds a series of linearly stacked pills with each pill being offset from an adjacent pill.

2. The device of claim 1, wherein the authentication sensor comprises:
    a camera;
    a fingerprint reader; or
    a photo detector.

3. The device of claim 1, wherein the medication dispenser comprises:
    a drug cartridge that receives, holds, and stages dosages for dispensing.

4. The device of claim 3, wherein the drug cartridge comprises:
    a spring-loaded magazine that receives, holds, and stages a plurality of pills for dispensing.

5. The device of claim 1, further comprising:
    a memory that stores data and control signals when a communication link is determined to be inactive.

6. A method for dispensing drugs, comprising:
    loading patient data and medication data of a user into a BECDD device comprising a camera;

installing a drug cartridge into the BECDD device, the drug cartridge comprising a spring-loaded dispenser configured to hold a series of linearly stacked pills with each pill being offset from an adjacent pill;

confirming completion of loading of the patient data and medication data into the BECDD device;

using the camera, sensing authentication data of the user that is used by the BECDD device to match the user data with the patient data and the medication data in the BECDD device;

confirming installation of drug cartridge into the BECDD device;

determining a ready-to-use status of the BECDD device; and delivering the ready-to-use BECDD device to the user.

7. The method of claim 6, further comprising:

sensing authentication data for the user; and sending the authentication data to a delivery control monitoring station (DCMS) for verification of the authentication data for the user.

8. The method of claim 6, further comprising:

setting a dosage interval.

9. The method of claim 8, further comprising:

authenticating the user based on the authentication data.

10. The method of claim 9, further comprising:

correlating a set dosage schedule to the medication data; and validating the dose schedule.

11. The method of claim 10, further comprising:

dispensing a dosage based on the validated dose schedule.

12. A method of dispensing drugs, comprising:

identifying an exceptions event;

generating exceptions data related to the exceptions event including an indication of a failure to take medication, an indication of a tamper event, or an indication of attempting to take medication too frequently;

sending the exceptions data to a computer located at a remote location; and receiving a control signal from the remote computer to display a message or generate a sound on a biometric electronic communicating drug dispenser device (BECDD) device, the BECDD device being generally rectangular in shape and comprising a generally rectangular cartridge configured to dispense a series of linearly stacked pills through a single dispensing opening at a base of the BECDD, the cartridge comprising a spring-loaded dispenser that holds the series of linearly stacked pills with each pill being offset from an adjacent pill, wherein the exceptions data is stored at the remote computer and associated with the BECDD device.

13. The method of claim 12, further comprising:

controlling an operation of the BECDD device based on the control signal.

14. The method of claim 13, wherein the operation comprises:

powering down the BECDD device;

powering up the BECDD device;

dispensing a dosage from the BECDD; or disabling the BECDD device.

15. The method of claim 12, wherein the exceptions data comprises:

identification data that identifies a person trying to access a dosage, including:

a fingerprint, a photo, a voice signature, or a retina image;

a time-stamp that includes a date and time of the exceptions event.

16. The method of claim 12, further comprising:

sending a second message related to the exceptions data to another computer, which may be located remotely from said remote computer.

17. The device of claim 1, wherein an image taken by the camera is sendable to the remote computer.

18. The device of claim 1, wherein the generally rectangular shaped housing comprises the authentication sensor located on a first side of the housing and a display located on a second side of the BECDD.

19. The device of claim 18, wherein the medication dispenser dispenses a pill on a third side of the BECDD.

* * * * *